United States Patent
Lilga et al.

(10) Patent No.: US 10,260,156 B2
(45) Date of Patent: Apr. 16, 2019

(54) SYSTEM AND PROCESS FOR ELECTROCHEMICAL UPGRADING OF BIO-OILS AND BIOCRUDES

(71) Applicants: BATTELLE MEMORIAL INSTITUTE, Richland, WA (US); BATTELLE ENERGY ALLIANCE, LLC, Idaho Falls, ID (US)

(72) Inventors: Michael A. Lilga, Richland, WA (US); Asanga B. Padmaperuma, Richland, WA (US); Tedd E. Lister, Idaho Falls, ID (US); Eric J. Dufek, Ammon, ID (US); Lucia M. Petkovic, Idaho Falls, ID (US); Luis A. Diaz-Aldana, Idaho Falls, ID (US)

(73) Assignee: BATTELLE MEMORIAL INSTITUTE, Richland, WA (US)

( * ) Notice: Subject to any disclaimer, the term of this patent is extended or adjusted under 35 U.S.C. 154(b) by 237 days.

(21) Appl. No.: 15/078,784

(22) Filed: Mar. 23, 2016

(65) Prior Publication Data
US 2016/0281246 A1    Sep. 29, 2016

Related U.S. Application Data

(60) Provisional application No. 62/136,979, filed on Mar. 23, 2015.

(51) Int. Cl.
| | |
|---|---|
| *C07C 1/24* | (2006.01) |
| *C25B 3/04* | (2006.01) |
| *C25B 3/00* | (2006.01) |
| *C25B 9/08* | (2006.01) |
| *C25B 9/04* | (2006.01) |
| *C25B 15/02* | (2006.01) |
| *C25B 15/08* | (2006.01) |

(Continued)

(52) U.S. Cl.
CPC ............ *C25B 3/04* (2013.01); *C07B 31/00* (2013.01); *C07C 1/24* (2013.01); *C25B 1/04* (2013.01); *C25B 9/04* (2013.01); *C25B 9/08* (2013.01); *C25B 15/02* (2013.01); *C25B 15/08* (2013.01); *Y02E 60/366* (2013.01)

(58) Field of Classification Search
CPC .. C07C 1/24; C07C 41/18; C11B 3/00; C11B 3/005; C25B 3/04; C25B 9/08; C25B 9/04; C25B 15/02; C25B 15/08
See application file for complete search history.

(56) References Cited

U.S. PATENT DOCUMENTS

| | | | |
|---|---|---|---|
| 2,303,210 A | 11/1942 | Hales | |
| 3,684,669 A * | 8/1972 | Matthews | ............... C25B 3/04 205/463 |

(Continued)

OTHER PUBLICATIONS

Li, Z., et al., Mild electrocatalytic hydrogenation and hydrodeoxygenation of bio-oil derived phenolic compounds using ruthenium supported on activated carbon cloth, Green Chem, 14, 2012, 2450-2459.

(Continued)

*Primary Examiner* — Youngsul Jeong
(74) *Attorney, Agent, or Firm* — Derek H. Maughan (57) ABSTRACT

A system and process are disclosed for electrochemically upgrading bio-oils and bio-crudes that enhance yields of selected reduction products for subsequent production of bio-based fuels.

6 Claims, 11 Drawing Sheets

(51) Int. Cl.
   *C07B 31/00*   (2006.01)
   *C25B 1/04*    (2006.01)

(56) References Cited

U.S. PATENT DOCUMENTS

| 5,475,160 | A  | * | 12/1995 | Singleton | ................ | B01J 23/80 |
|---|---|---|---|---|---|---|
| | | | | | | 568/861 |
| 6,218,556 | B1 | * | 4/2001 | Pintauro | ................... | C11C 3/12 |
| | | | | | | 204/167 |
| 7,795,484 | B2 | * | 9/2010 | Koivusalmi | .............. | C07C 1/24 |
| | | | | | | 585/324 |

OTHER PUBLICATIONS

Benziger, J., et al., A Polymer Electrolyte Hydrogen Pump Hydrogenation Reactor, Ind Eng Chem Res, 49, 2010, 11052-11060.

Green, S. K., et al., Electrocatalytic Reduction of Acetone in a Proton-Exchange-Membrane Reactor: A Model Reaction for the Electrocatalytic Reduction of Biomass, ChemSusChem, 5, 2012, 2410-2420.

Saez, A., et al., Electrocatalytic hydrogenation of acetophenone using a Polymer Electrolyte Membrane Electrochemical Reactor, Electrochimica Acta, 91, 2013, 69-74.

Pintauro, P. N., et al., Electrochemical Hydrogenation of Soybean Oil with Hydrogen Gas, Ind Eng Chem Res, 44, 2005, 6188-6195.

Ono, S., et al., Electrolytic Reduction of Aromatic Carboxylic Acids. I. Reduction of Benzoic Acid under Pressure, Bulletin of the Chemical Society of Japan, 25, 1952, 404-407.

* cited by examiner

SYSTEM AND PROCESS FOR ELECTROCHEMICAL UPGRADING OF BIO-OILS AND BIOCRUDES

CROSS REFERENCE TO RELATED APPLICATIONS

This is a non-provisional application that claims priority from U.S. Provisional Patent Application No. 62/136,979 filed 23 Mar. 2015, which reference is incorporated in its entirety herein.

STATEMENT REGARDING RIGHTS TO INVENTION MADE UNDER FEDERALLY-SPONSORED RESEARCH AND DEVELOPMENT

This invention was made with Government support under Contract DE-AC05-76RL01830 and Contract DE-AC07-05ID14517 awarded by the U.S. Department of Energy. The Government has certain rights in the invention.

FIELD OF THE INVENTION

The present invention relates generally to processes for upgrading fast pyrolysis bio-oils and hydrothermal liquefaction biocrudes. More particularly, the invention relates to a system and process for electrochemically upgrading bio-oils and biocrudes.

BACKGROUND OF THE INVENTION

Bio-oils are complex microemulsions of aqueous and non-aqueous phases containing hundreds of different organic and inorganic compounds. Oxygenated hydrocarbons in bio-oils include esters, acids, aldehydes, alcohols, ketones, sugars, and various phenol derivatives. These reactive species in bio-oils complicate storage, transportation, and downstream processing because secondary reactions cause condensation and polymerization reactions which increase the viscosity of the bio-oil and form problematic solids. Bio-oils are also corrosive due to the presence of organic acids such as acetic acid and formic acid as well as phenolics that can damage the infrastructure of conventional processing systems. Bio-oils must therefore be upgraded before they can be introduced into fuel processing systems for processing into transportation fuels. Reactivity and lack of stability of bio-oils are well-known problems. These problems are attributed to reactions involving acids, aldehydes, sugars, and phenols. For example, organic acids can form esters by reaction with alcohols or olefins, can catalyze condensation reactions, and can cause corrosion. Aldehydes can oligomerize or react with phenols to form resins. Removal of these reactive functionalities can thus improve bio-oil stability. Stabilization of bio-oils by hydrogenation is typically performed using pressurized $H_2$ at elevated temperatures. However, bio-oils lack thermal stability. And, upon break down, compounds in bio-oils form coke which blocks catalyst sites and plugs reactors during treatment at elevated temperatures. These issues have yet to be resolved.

Accordingly, new systems, processes, and catalysts are needed to upgrade bio-oils under mild conditions, to reduce reactive functionalities to more stable compounds, to reduce corrosivity of the bio-oil, and to increase carbon and hydrogen efficiency of bio-oil processing, e.g., into bio-based transportation fuels. The present invention addresses these needs.

SUMMARY OF THE INVENTION

The present invention includes an electrolysis system configured with an electrolysis cell (electrolyzer) for performing electrochemical hydrogenation (ECH) of bio-oils and biocrudes, and a process for upgrading (hydrotreating) pyrolysis bio-oils and upgrading biocrudes obtained from hydrothermal liquefaction processing. The electrolysis system performs electrochemical hydrogenation (ECH) that reduces reactive functionalities in the bio-oils and biocrudes, and removes small organic acids, water, chloride, and other ash components from the bio-oils and biocrudes that reduces corrosivity and yields more stable compounds. In some embodiments, the electrolysis system includes a single membrane cell. In some embodiments, the electrolysis system includes a dual membrane cell.

The ECH process includes introducing a feed containing a bio-oil or a biocrude into an electrolysis cell that includes at least one ion-selective membrane; and then passing a current through the electrolysis cell to convert molecules in the feed to a reduction product. The reduction product includes reduced molecules containing a higher proportion of hydrogen than the feed molecules. The ECH process uses protons and water as a hydrogen source. The ECH process reduces reactive functionalities and forms more stable compounds. The system and process increase carbon and hydrogen efficiency and provide a new approach for conversion of bio-oils into transportation fuels. The process may include introducing the bio-oil and/or the biocrude to a cathode. Hydrogen obtained in the reduced molecules may be derived from conversion of water and/or conversion from protons. The reduced product includes a total acid number less than the total acid number of the feed.

In some embodiments, the electrolysis cell includes a catalyst on one or more of the ion-selective membranes.

In some embodiments, the feed is introduced continuously into the electrolysis cell. In some embodiments, the feed is introduced into the electrolysis cell periodically, for example, in individual or separate batches. In some embodiments, the feed is processed in an electrolysis cell that is a polymer electrolyte membrane (PEM) cell. The feed may be introduced into the electrolysis cell with a pressurized gas containing hydrogen that is delivered to the cathode of the electrolysis cell. The feed may be introduced into the electrolysis cell with a pressurized gas containing hydrogen that is delivered to the anode of the electrolysis cell. The hydrogen delivered with the feed into the electrolysis cell may be obtained from an external pressure source, from hydrogen gas evolved at the cathode, or a combination of these sources.

Current may be passed into the electrolysis system by applying a controlled potential or a controlled current. Current may also be passed by applying a pulsed potential or a pulsed current. Current may also be passed by applying a ramped potential or a ramped current. In some embodiments, passage of current transfers anions and protons into a concentrate stream located between at least two ion-selective membranes (e.g., cation-exchange and anion-exchange membranes) that removes acids from the bio-oil, for example, by dialysis. Passage of current may also separate water from the feed. Passage of current may also separate inorganic anions from the feed.

The process may include converting phenol groups in feed molecules to reduced molecules that include alcohol-containing molecules. The alcohol-containing molecules may be deoxygenated by dehydrating the alcohol-containing molecules to form olefins. The process may include converting ether-containing phenol molecules in the feed to reduced molecules that include aliphatic ether-containing molecules. The process may include converting aromatic rings in feed molecules to reduced molecules that include aliphatic-containing molecules. The process may include converting olefin-containing molecules in the feed to reduced molecules that include aliphatic-containing molecules. The process may include converting carbonyl groups in feed molecules to reduced molecules that include alcohol-containing groups. The reduced molecules containing alcohol groups may be further reduced to form deoxygenated molecules. The feed may be introduced into an electrolysis cell without addition of a supporting electrolyte.

The feed may be introduced into an electrolysis cell that includes two electrodes (e.g., cathode and anode) that are separated by a cation-exchange membrane without need of a supporting electrolyte. The feed may be introduced into an electrolysis cell that includes two electrodes (e.g., cathode and anode) that are separated by a cation-exchange membrane and an anion-exchange membrane without need of a supporting electrolyte.

The process may further include recycling the reduced product containing the higher proportion of hydrogen to the same electrolysis cell or one or more additional electrolysis cells to further increase the proportion of hydrogen in the reduced product. The process may further include passing the reduced product through a thermal hydrotreating reactor to further increase the proportion of hydrogen in the reduced product. The process may further include passing the reduced product through a thermal alcohol dehydration reactor to decrease the oxygen content in the reduced product. The process may further include passing the reduced product to a thermal alkylation reactor to increase the average molecular weight of the reduced product.

The purpose of the foregoing abstract is to enable the United States Patent and Trademark Office and the public generally, especially the scientists, engineers, and practitioners in the art who are not familiar with patent or legal terms or phraseology, to determine the nature and essence of the technical disclosure of the application. The abstract is neither intended to define the invention of the application, which is measured by the claims, nor is it intended to be limiting as to the scope of the invention in any way.

DETAILED DESCRIPTION

The present invention includes an electrolysis system, electrolysis cell (electrolyzer), and process for upgrading (hydrotreating) bio-oils obtained from pyrolysis, and biocrudes obtained from hydrothermal liquefaction processing. In the following description, for purposes of brevity, bio-oils and biocrudes will be referred to as bio-oils or oils. In the following description, embodiments of the present invention are shown and described by way of illustration for carrying out the invention. It will be apparent that various modifications, alterations, and substitutions to the present invention may be made. The present invention is intended to cover all modifications, alternative constructions, and equivalents falling within the spirit and scope of the invention defined in the claims. Therefore the description should be seen as illustrative and not limiting.

Figure 1:
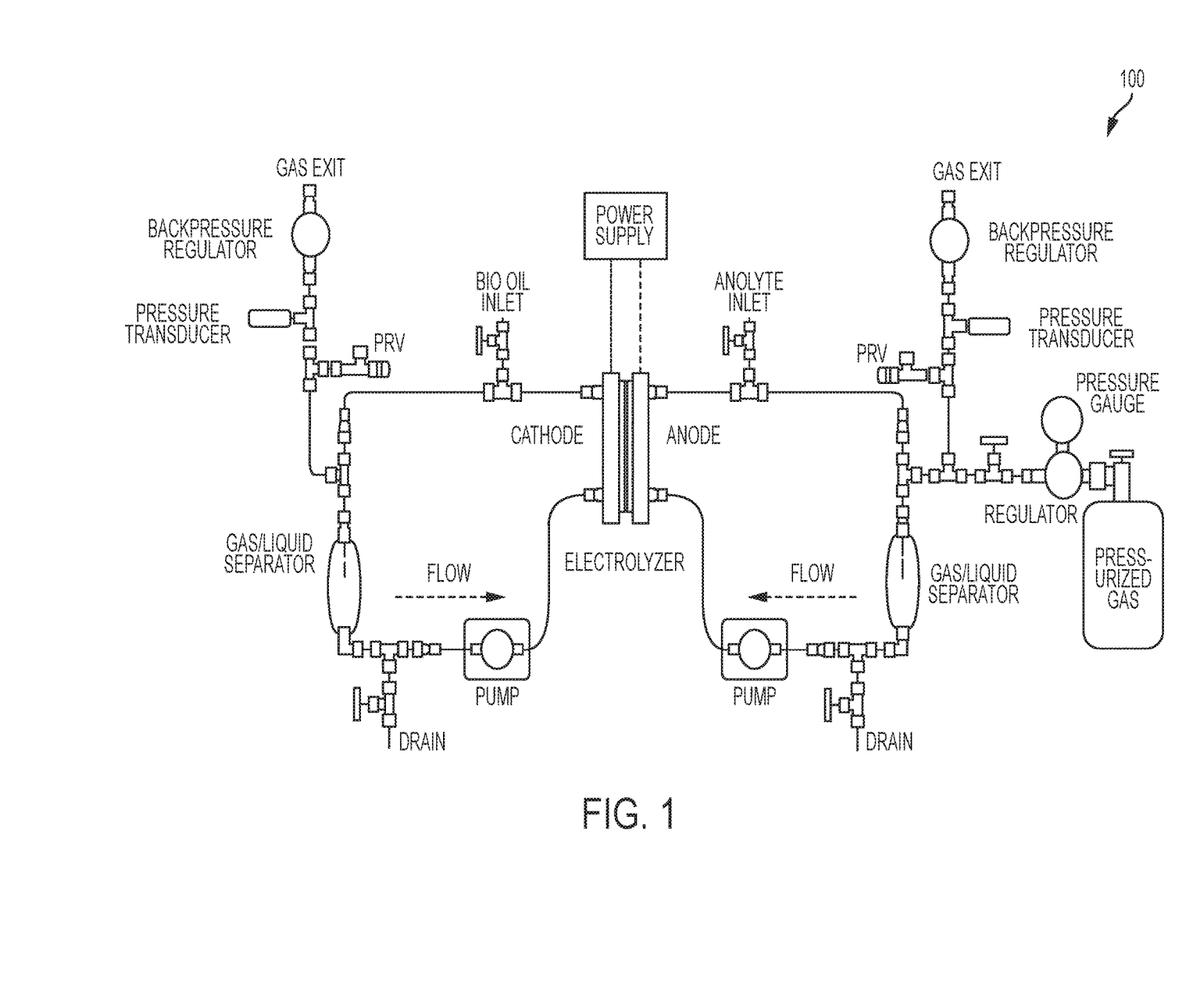
FIG. 1 shows an exemplary electrochemical system for hydrogenating bio-oils and biocrudes, according to one embodiment of the present invention.

FIG. 1 shows an exemplary electrolysis system 100 configured with an electrolyzer that includes a cathode in a cathode chamber and an anode in an anode chamber. In some embodiments, the electrolyzer is of a polymer electrolyte membrane (PEM) cell design. The system brings a bio-oil into contact with the cathode in the cathode chamber of the electrolyzer, and an anolyte into contact with the anode in the anode chamber of the electrolyzer. The cathode chamber and the anode chamber in the electrolyzer may be separated by either one or two membranes that are contained in a membrane electrode assembly (MEA). When the MEA contains a single membrane (i.e., a single membrane cell), the membrane is a cation exchange membrane (CEM). When the MEA contains two membranes (i.e., a dual membrane cell), one of the membranes is CEM; the other membrane is an anion exchange membrane (AEM). Single and dual membrane cells are described further below. Electrolysis system 100 is designed to operate at atmospheric pressure or elevated pressure. At atmospheric pressure, gases generated in the system are released through devices including but not limited to, for example, backpressure regulators or other like devices. At elevated pressure, cathode and anode chambers are pressurized prior to an experiment and/or gases generated during the experiment are retained. In the elevated pressure system, each chamber may independently include a backpressure regulator to control system pressure, a pressure transducer, and a pressure-relief valve (PRV) positioned in the gas phase headspace of each chamber. Gas/liquid separators may be positioned to act as main reservoirs for fluids and to separate the liquid phase from the gas phase headspace. Solutions may be added, for example, through an inlet port, and removed through a drain located in the lowest part of the system. In the exemplary system shown in the figure, solutions may be pumped continuously through the electrolyzer, for example, in a recycle mode. In other embodiments (not shown), solutions may be pumped from one electrolyzer to one or more electrolyzers positioned in series to further hydrogenate the bio-oil, for example, in a continuous flow mode.

Electrolysis System 100 can be operated as a self-pressurized system to limit escape of $H_2$ gas formed during reduction of protons and water within the cathode chamber, and to provide other advantages for conversion of bio-oils described herein. Pressures attainable in the system are limited only by the materials of construction. Typical operation pressures are from about 100 psi to about 500 psi. Higher pressures may also be used with compatible materials and suitable construction. Pressurized operation increases the concentration of dissolved $H_2$ in the bio-oil. The increased $H_2$ concentration shifts the equilibrium for $H_2$ production and shifts the Nernst potential for the $H_2$ evolution reaction to more negative potentials, thereby increasing the reduction potential attainable at the cathode.

Electrolysis System 100 reduces reactive oxygenated compounds such as the aldehydes, e.g., as depicted in chemical and electrochemical (EC) reactions [1]-[5], as follows:

EC cathode: $2H^+ + 2e^- \rightarrow 2H_{ads}$ [1]

EC anode: $H_2O \rightarrow \frac{1}{2}O_2 + 2H^+ + 2e^-$ [2]

Surface reaction: $2H_{ads} + \text{aldehyde} \rightarrow \text{alcohol}$ [3]

Dehydration: $\text{alcohol} \rightarrow \text{olefin} + H_2O$ [4]

Net reaction: $\text{aldehyde} \rightarrow \text{olefin} + \frac{1}{2}O_2$ [5]

In net reaction [5], $H_2$ does not appear in the balanced equation. As an example, aldehydes may be deoxygenated to produce $O_2$ and an olefin product. Reactions [1]-[5] may employ an adsorbed hydrogen atom (Haas) generated at the cathode surface as a reactive species. However, reactive species may alternately involve other protonated or electrochemically reduced organics. Reactions [1]-[5] may employ an aldehyde, for example, but reactions can also reduce other oxygenates including, for example, ketones and phenolics. In reaction [4], alcohol intermediates can be dehydrated to olefins. Dehydration reactions may be conducted internal to the cell, or in a downstream reactor. The degree to which these ideal equations can be realized depends on reaction efficiencies at the selected electrodes. Self-pressurization with $H_2$ can increase the ECH reaction versus $H_2$ formation through equilibrium forces.

Figure 2:
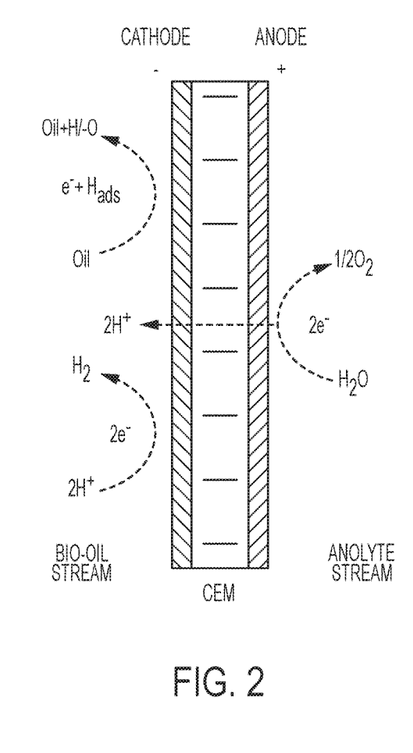
FIG. 2 shows an exemplary electrolyzer configured with a single membrane cell for electrochemical hydrogenation of bio-oils and biocrudes in concert with the present invention.

FIG. 2 shows an exemplary electrochemical cell (electrolyzer) configured with a single exchange membrane, according to one embodiment of the present invention. In the figure, the electrolyzer includes at least two electrodes, a cathode (labelled with a minus sign) and an anode (labelled with a plus sign with each electrode positioned in a separate cell chamber. Electrodes and electrolyzers are fabricated as will be understood by those of ordinary skill in the art. Each electrode is separated from the other electrode by a single exchange membrane, for example, a cation-exchange membrane (CEM). The cathode and anode are in electronic and ionic contact. The cathode and anode are attached to opposite sides of the CEM. The electrodes are separated only by the membrane in a zero-gap configuration. The zero-gap configuration minimizes voltage drop between the electrodes and eliminates the need to add a supporting electrolyte to the bio-oil.

In some embodiments, the cathode and anode are bonded to the membrane. In other embodiments, the electrodes are physically pressed against the membrane.

In yet other embodiments, the electrodes are physically separated from the membrane. Electrodes described herein may be comprised of, or include, various selected materials and compositions including, but not limited to, for example, metals, carbons, various metals on carbon supports, various metal oxides on carbon supports or metal supports, various conductive composite materials, and combinations of these various materials as will be understood by those of ordinary skill in the electrochemical arts. No limitations are intended.

In the figure, chemical reactions and the flow path of protons are shown at each electrode. The CEM binds negative functional groups, allowing protons to pass.

In the present invention, electrolysis in the single membrane cell includes applying a potential to the electrodes that is sufficiently high to cause electrons to flow to, or from, molecules present in the electrolyzer. In operation, a sufficiently high potential during electrolysis may be attained by controlling either the applied potential or the applied current that flows through the electrolyzer. Ideally, electrons flow to molecules of the bio-oil in preference to water or acid.

In other embodiments, potentials and currents delivered to the electrolyzer may be steady, ramped, or pulsed.

In the exemplary embodiment, the cathode half-cell reaction provides reduction of bio-oil molecules and the anode half-cell reaction provides oxidation of water, but the invention is not limited thereto. For example, in other embodiments, the anode reaction may provide other oxidation reactions including, for example, oxidation of $H_2$ such as that formed in excess at the cathode; oxidation of organics, for example, for wastewater treatment; oxidation that forms products such as ketones, or oxidation of chloride to chlorine gas. No limitations are intended.

Figure 3:
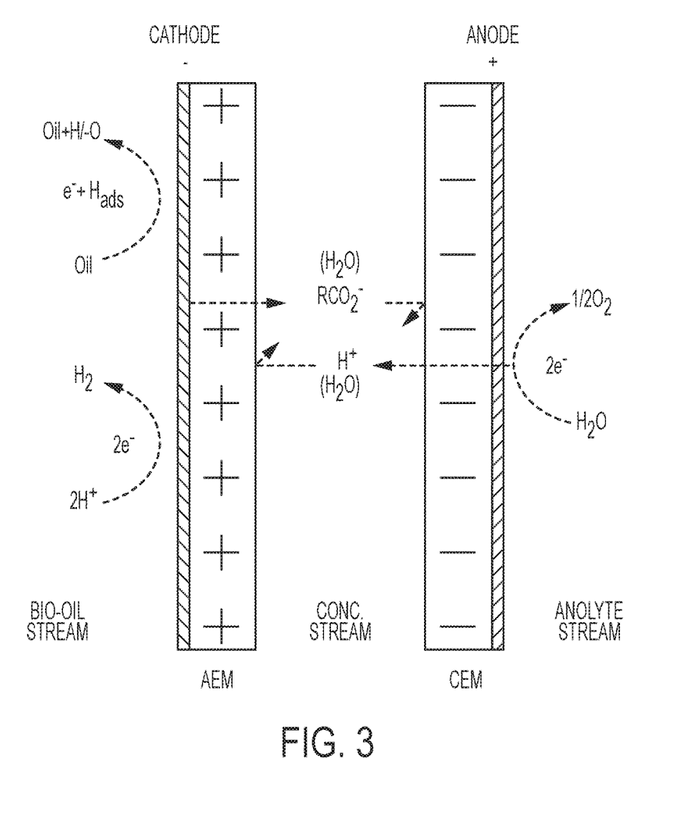
FIG. 3 shows an exemplary electrolyzer configured with a dual membrane cell for electrochemical hydrogenation of bio-oils and biocrudes and for electrodialytic separation of acids in concert with the present invention.

FIG. 3 shows another exemplary electrolyzer for simultaneous electrochemical hydrogenation and separation, according to another embodiment of the present invention. In the figure, the electrolyzer includes dual ion-selective membranes, a CEM and an anion exchange membrane (AEM). The electrodes are bonded to respective membranes to create a zero-gap configuration. The cathode is bound to the AEM and the anode is bound to the CEM. In operation, the AEM binds positive functional groups and allows anions to pass. The CEM and AEM are configured to control ion and chemical flow for electrochemical separation of short-chain organic acids, chloride ($Cl^-$), and water from bio-oils. As shown in the figure, in the instant configuration, the cathode and anode are separated by a center chamber containing a concentrate stream which offers processing advantages described further herein.

In the dual membrane configuration, electrical charge injected into the bio oil from the cathode is compensated for by movement of anions from the bio-oil [including, e.g., short organic acids such as acetic acid or chloride ($Cl^-$)] through the AEM into the concentrate stream between the two membranes. Protons generated at the anode, for example, during oxidation of water to $O_2$, move through the CEM into the concentrate stream. The overall result of anion and proton movement results in collection of acids in the concentrate stream. Protons in the bio-oil may be consumed by generation of $H_2$ and ECH of organics, which increases pH and decreases corrosivity of the bio-oil. Water and small organic molecules in the bio-oil can migrate in the direction of the flow of charge due to electro-osmotic drag. With proper selection of such characteristics as AEM pore size and/or other properties, the AEM can effectively separate short-chain organics, $Cl^-$, and water from the bio-oil. Organic acids collected in the concentrate stream may be processed for selected commodity uses or sent to a reformer (not shown) should $H_2$ be needed for downstream processing.

Figure 4A:
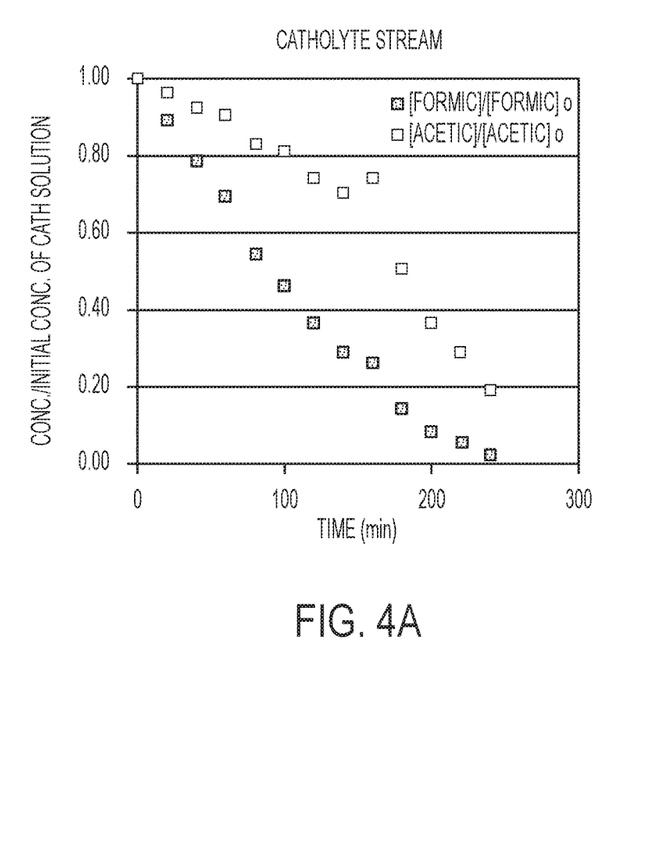
FIGS. 4A-4B plot ratios of selected catholyte concentrations in exemplary catholyte solutions processed in a dual membrane electrochemical cell as a function of time.
Figure 4B:
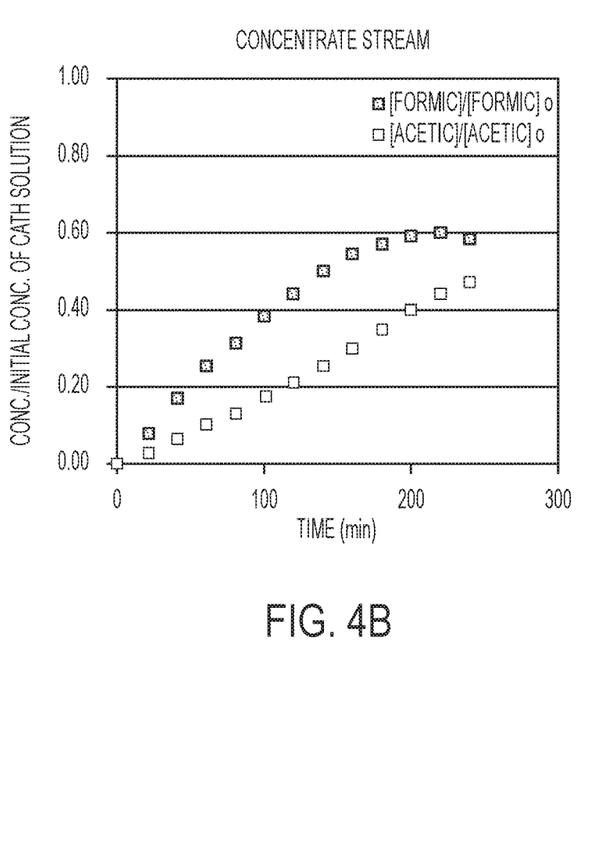
Figure 5A:
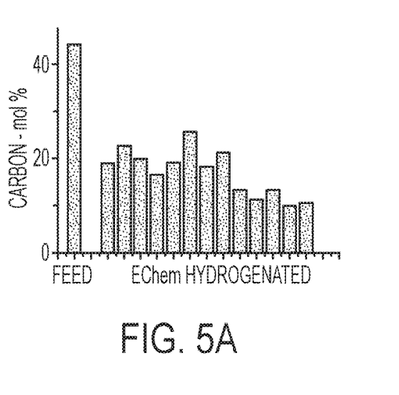
FIGS. 5A-5D plot carbon mole % values for aromatics and phenols (5A), aliphatics (5B), alcohols and ethers (5C), and carbonyls (5D) for a bio-oil feed against an electrochemically treated bio-oil.
Figure 5B:
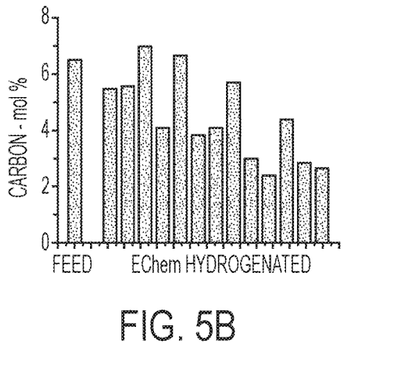
Figure 5C:
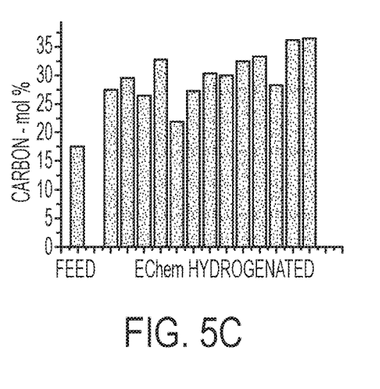
Figure 5D:
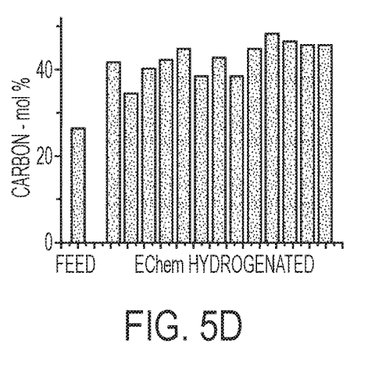

FIGS. 4A-4B plot the ratio of the concentration (measured to initial) of selected catholyte compounds (formic acid and acetic acid) in the catholyte stream against the same compounds in the concentrate stream, respectively. Catholyte solutions were processed in a dual membrane electrochemical cell as a function of time. The system of FIG. 1 and the electrolyzer of FIG. 3 were used. EXAMPLE 2 presents further details. Data in FIG. 4A show that the concentrations of formic and acetic acids decrease from the catholyte (feed) stream as a function of time. Data in FIG. 4B show that concentrations of formic and acetic acid increase in the concentrate stream as a function of time. Results demonstrate that the system separates the compounds from the feed.

Electrodes used in single and dual membrane cells described herein may be purchased commercially (e.g., Giner, Inc., Newton, Mass., USA), or may be constructed using methods known in the art. For example, for the dual membrane cell, an anode can be prepared as a sintered titanium (Ti) metal film with a platinum (Pt) coating formed by electroplating. The anode may then be hot pressed onto a CEM. A representative CEM may be a NAFION-117® sheet (Dupont, Wilmington, Del., USA). The cathode may be installed onto an AEM sheet by applying a catalyst mixture comprising 20% palladium (Pd) metal on a carbon support in a 5% NAFION® ionomer solution (Dupont, Wilmington, Del., USA) diluted in methanol. The catalyst mixture and cathode metal may be attached to the AEM by hot pressing. A representative AEM may be a material such as EXCELLION™ (SnowPure, San Clemente, Calif., USA). Construction details and composition variations, including different metal catalysts, are known in the art and are not meant to be limiting.

The present invention provides electrochemical hydrogenation processing of raw bio-oils for the first time. The electrochemical system includes a cell configuration with electrodes physically attached to a pair of membranes in an electrodialysis configuration. The system configuration eliminates need for addition of supporting electrolytes to the bio-oil, which minimizes the applied potential. In addition, the cell may be self-pressurized using $H_2$ generated within the cell to enhance hydrogenation. Membranes in the electrochemical cell separate acids and water and reduce total acid number of bio oils. The configuration allows collection of acids for use as commodity chemicals or for reforming if downstream $H_2$ is needed. Eliminating water from the bio-oil reduces transportation costs and improves the efficiency of downstream processes.

The ECH process of the present invention also reduces acidity of the bio-oil through proton reduction and dialysis separation. For example, reduction in acidity can be expected to improve bio-oil stability and allow transportation of the treated bio-oil to centralized or other processing facilities. In addition, removal of small acids and other small molecules by dialysis prevents them from being sent to a downstream hydrotreater. Hydrogenation of small molecules in conventional processing wastes valuable $H_2$ and generates light gases that need to be separated, collected, or flared.

Results show the electrochemical process of the present invention also allows hydrotreating of bio-oils (with a reduction in phenolics and carbonyls in the bio-oil) to be conducted at lower temperatures (40° C. to about 80° C.) and at pressures less than about 300 psi ($2.1 \times 10^3$ kPa) than required for conventional thermal catalytic reduction approaches (i.e., 140° C. to 425° C. and pressures of between 1200 psi ($8.3 \times 10^3$ kPa) to 2000 psi ($1.4 \times 10^4$ kPa), and multiple stages of reduction to hydrotreat bio-oils without coke formation.

Systems and processes of the present invention may change currently accepted flowsheets for upgrading bio-oil. For example, ECH reduction of phenolics and carbonyls in bio-oil at these moderate conditions has the potential to completely change currently accepted staged thermal catalytic approaches. For example, the extent of reduction of phenols was unexpected. A reduction in phenolics of about 50% was observed by product analyses. However, more extensive reduction can be expected with variations to the system such as using multiple electrolyzers in series and parallel, increasing contact time between the bio-oil and the electrode, and improving hydrodynamics within the electrolyzer to ensure good mixing and contact with the electrode. Phenols are difficult to reduce thermally in conventional processing.

ECH of the present invention may also eliminate need for one or more hydrodeoxygenation (HDO) stages, may eliminate corresponding catalyst costs, and may therefore reduce overall capital expenditures. In cases where ECH-treated bio-oils require further thermal hydrotreating, the ECH-treated bio-oil and pressurized $H_2$ exiting the electrochemical cells may be fed to an external reactor where thermal catalytic hydrotreating may be conducted. Thus, the present invention can employ electrochemically generated $H_2$ in the process thereby minimizing need for $H_2$ from external supplied sources including, e.g., $H_2$ from natural gas reforming.

ECH-treated bio-oils exiting the electrochemical cells may also be fed to other thermal reactors where other conversions may be carried out. For example, feeding ECH-treated bio-oils to an alkylation reactor may increase the average molecular weight of the reduced product, thereby increasing the fraction of the oil in the distillate range, for example by reacting alcohols with phenolics. As another example, feeding ECH-treated bio-oils to an alcohol dehydration reactor may deoxygenate the oil by removal of water to form olefins. Any or all of the external hydrotreating, alkylation, and dehydration reactors may be used in any order.

The following Examples provide a further understanding of the present invention.

Example 1

Electrochemical Hydrogenation 10 mL of bio-oil was added to the cathode chamber. 20 mL of purified water was added to the anode chamber. A direct current (DC) power supply delivered a constant current to the electrolyzer. The pressure increased gradually in the cathode chamber as $H_2$ was generated (i.e., self-pressurized). The anode chamber containing water was maintained approximately 15 psi above the cathode pressure using both self-generated $O_2$ and argon gas supplied from an external argon gas supply. A potential versus time curve during a 6 hour reaction at 0.95 amps (i.e., 0.95 A) shows a very flat profile indicating stable operation observed in all runs. TABLE 1 lists experimental conditions from several experiments performed to test electrochemical hydrogenation of bio-oil. Experimental conditions including the cathode catalyst, current density, time, and temperature were varied. Values for maximum pressure are those recorded at the end of the experiments given that pressure was allowed to increase over the course of the experiments from generated $H_2$.

TABLE 1

| Run # | Run Date | Electrode | Current (A) | Time (hours) | Temp (° C.) | Max Pressure (psi) |
|---|---|---|---|---|---|---|
| Run # 1 | Oct. 15, 2014 - C | Au | 0.95 | 2 | 23.5° C. | 192 |
| Run # 2 | Oct. 21, 2014 - C | Au | 0.95 | 2 | 48.4-40.8 | 155 |
| Run # 3 | Oct. 23, 2014 - C | Au | 0.95 | 2 | 78.3-57.7 | 126 |
| Run # 4 | Oct. 24, 2014 - C | Au | 0.475 | 4 | 43.2-40.1 | 119 |
| Run # 4 | Oct. 29, 2014 - C | Au | 0.2375 | 8 | 39.6-40.8 | 90 |
| Run # 5 | Nov. 18, 2014-C | Pd | 0.95 | 2 | 39.3-40.7 | 159 |
| Run # 6 | Nov. 19, 2014-C | Pd | 0.95 | 2 | 22.2-24.2 | 171 |
| Run # 7 | Nov. 20, 2014-C | Pd | 0.475 | 4 | 23.5-24.0 | 131 |
| Run # 8 | Nov. 21, 2014-C | Pd | 0.475 | 4 | 40.3-39.9 | 106 |
| Run # 9 | Dec. 10, 2014-C | Pd | 0.95 | 2 | 59.6-60.3 | 77 |
| Run # 10 | Dec. 17, 2014-C | Pd | 0.2375 | 8 | 60.8-59.0 | 125 |
| Run # 11 | Dec. 19, 2014-C | Pd | 0.95 | 2 | 60.6-60.0 | 162 |
| Run # 12 | Jan. 12, 2015-C | Pd | 0.95 | 6 | 39.6-40.9 | 213 |
| Run # 13 | Jan. 14, 2015-C | Pd | 0.95 | 6 | 39.6-41.0 | 322 |

Example 2

Separation

Experiments were performed with a dual membrane cell (see FIG. 3) employing both an AEM and a CEM on surrogate mixtures containing formic acid and acetic acid (5% acetic acid and 3% formic acid) in water as representative systems for pyrolysis oils. The center compartment was filled with a concentrated stream containing 10 mL solution of 1 M $Na_2SO_4$. The anode solution was 10 mL of purified water. A constant current of 0.1 A was applied to the cell during operation. Cell voltage was recorded. Experiments were performed for a time between 1 to 4 hours. Solutions were collected after operation and volume and mass were recorded and compared to initial values. pH was also recorded before and after operation. A sample of each solution was analyzed for acetic and formic acid.

FIGS. 4A-4B plot data obtained from experiments in which surrogate mixtures containing acetic acid and formic acid (i.e., catholytes), concentrates, and anolytes were sampled at regular intervals and analyzed. Data in the figures show a progression in the concentration of acetic acid and formic acid concentrations (anolyte data are not shown due to the low values). Data are presented as a ratio to the original catholyte concentration. Formic and acetic acid concentrations drop in the catholyte with time and build in the concentrate which demonstrates the anticipated separation function of the system. Formic acid transport is favored over acetic acid. pH of the catholyte increased from 1.90 to 4.20, showing removal of acids from the feed, while pH of the concentrate decreased from 6.22 to 2.17, showing the concentration of acids in the concentrate stream. The ratio in the concentrate is lower due to a volume increase from water transport.

Example 3

Product Analysis

Figure 6:
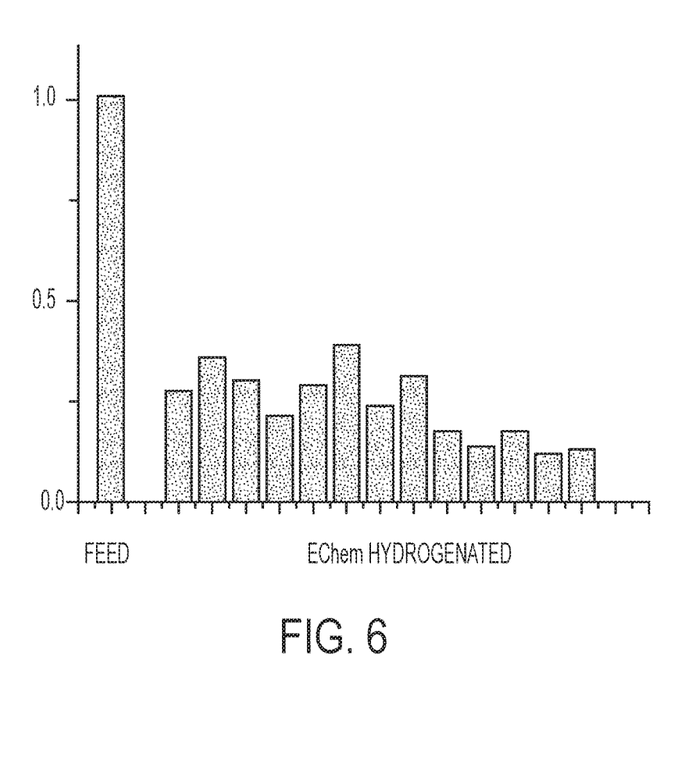
FIG. 6 plots mole ratio of aromatics to aliphatics for a bio-oil feed against an electrochemically treated bio-oil.
Figure 7A:
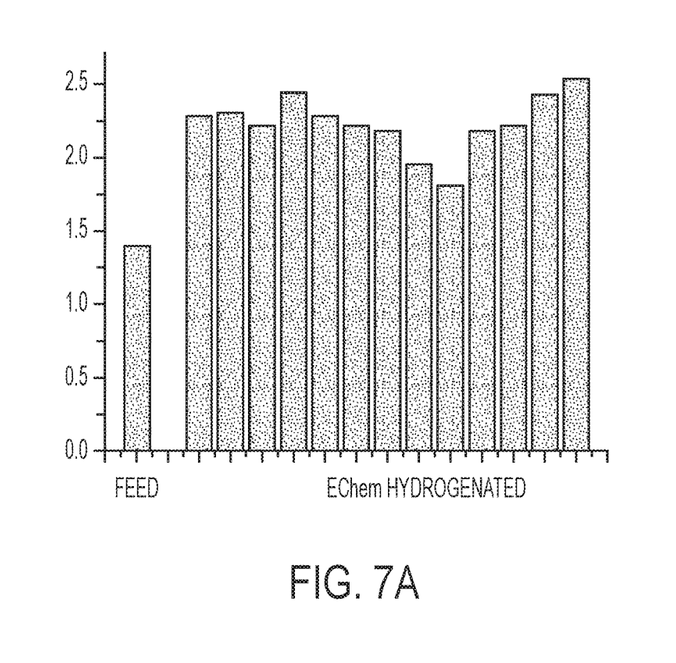
FIGS. 7A-7B plot hydrogen-to-carbon ratio (7A) and oxygen-to-carbon ratio (7B) for a bio-oil feed against an electrochemically treated bio-oil.
Figure 7B:
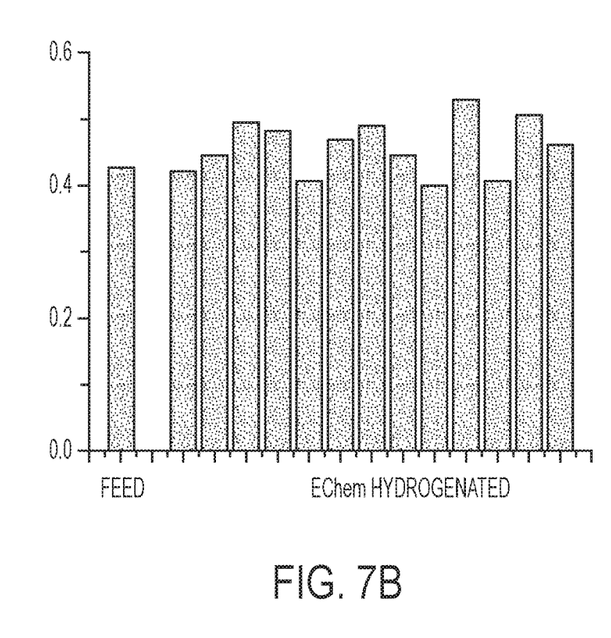
Figure 8A:
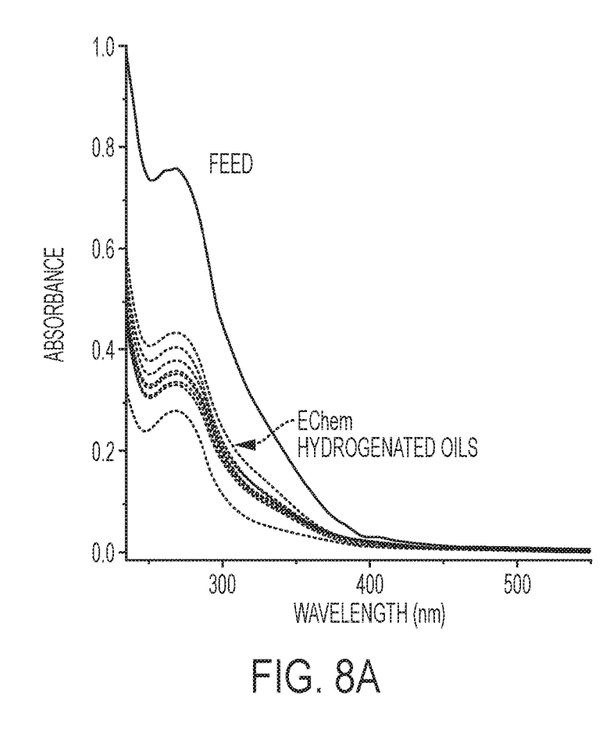
FIGS. 8A-8B plot UV/VIS Spectra (8A) and hydrogen-to-carbon ratio as a function of UV/VIS absorbance (8B) for a bio-oil feed against an electrochemically treated bio-oil.
Figure 8B:
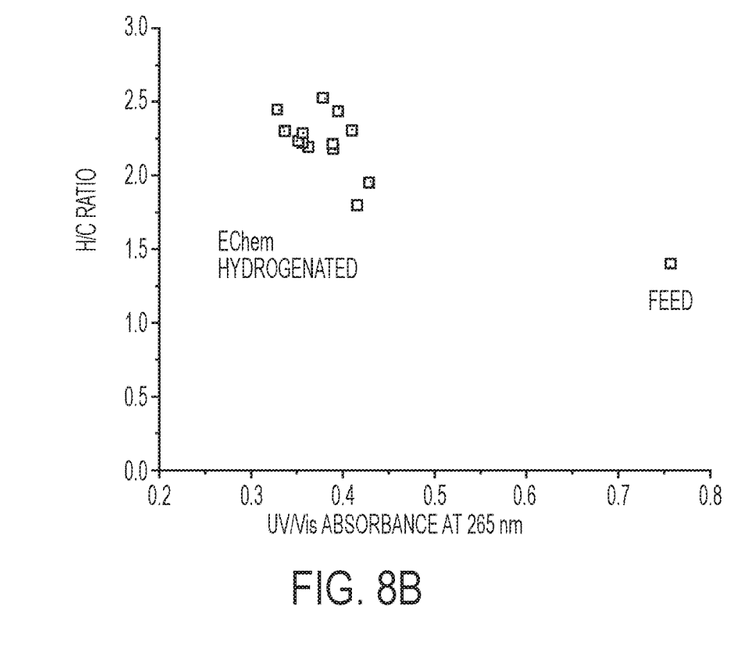
Figure 9:
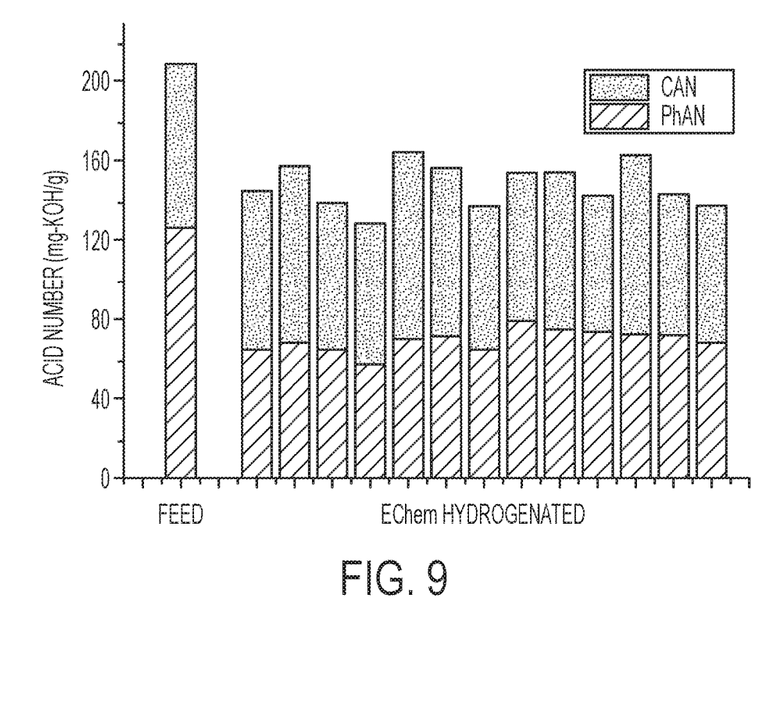
FIG. 9 plots carboxylic acid number (CAN), phenolic acid number (PhAN), and total acid number (TAN=CAN+PhAN) for a bio-oil feed against an electrochemically treated bio-oil.
Figure 10:
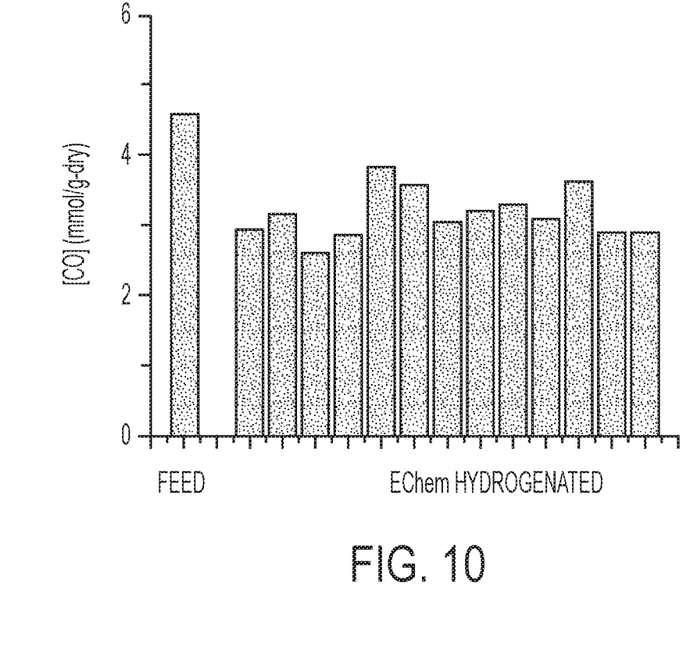
FIG. 10 plots carbonyl concentration for a bio-oil feed against an electrochemically treated bio-oil.

Bio-oil samples electrochemically treated in the single-membrane cell (FIG. 2) were analyzed using several methods including, e.g., NMR, UV-VIS, elemental analysis, Karl Fisher titration, acid titration, and determination of carbonyls by a reaction/titration method. TABLE 2 summarizes the $^{13}C$ NMR data. Data are shown graphically in FIG. 5 and FIG. 6.

| | % Carbon, by $^{13}C$ NMR | | | | | | | | | | |
|---|---|---|---|---|---|---|---|---|---|---|---|
| Run # | Carbonyl (220-200) | Carboxyl (185-170) | Phenolic (170-142) | Aromatic (142-95) | Alcohols (95-62) | Ether (62-45) | Total Aliphatic (35-0) | Ether + Alcohol (95-45) | $sp^2$ (170-95) | $sp^3$ (95-0) | $sp^2/sp^3$ |
| FP-Feed | 6.49 | 5.69 | 13.78 | 30.32 | 21.66 | 4.55 | 17.51 | 26.21 | 44.10 | 43.72 | 1.01 |
| Run # 2 | 5.46 | 6.44 | 6.79 | 12.38 | 19.31 | 22.11 | 27.50 | 41.42 | 19.17 | 68.92 | 0.28 |
| Run # 3 | 5.54 | 7.61 | 10.35 | 12.56 | 17.65 | 16.70 | 29.59 | 34.35 | 22.91 | 63.94 | 0.36 |
| Run # 4 | 6.94 | 6.31 | 7.71 | 12.43 | 20.14 | 19.97 | 26.50 | 40.11 | 20.14 | 66.61 | 0.30 |
| Run # 5 | 4.05 | 4.62 | 5.59 | 10.89 | 19.95 | 21.97 | 32.94 | 41.92 | 16.48 | 74.86 | 0.22 |
| Run # 6 | 6.58 | 7.62 | 4.63 | 14.47 | 26.96 | 17.87 | 21.87 | 44.83 | 19.10 | 66.70 | 0.29 |
| Run # 7 | 3.80 | 5.32 | 6.57 | 18.75 | 24.10 | 14.09 | 27.37 | 38.19 | 25.32 | 65.56 | 0.39 |
| Run # 8 | 4.06 | 4.84 | 6.65 | 11.51 | 23.20 | 19.32 | 30.42 | 42.52 | 18.16 | 72.94 | 0.25 |
| Run # 9 | 5.62 | 4.94 | 7.87 | 13.27 | 21.86 | 16.24 | 30.21 | 38.10 | 21.14 | 68.31 | 0.31 |
| Run # 10 | 2.95 | 6.40 | 4.56 | 8.82 | 26.36 | 18.39 | 32.52 | 44.75 | 13.38 | 77.27 | 0.17 |
| Run # 11 | 2.36 | 4.86 | 4.00 | 7.20 | 23.42 | 24.70 | 33.46 | 48.12 | 11.20 | 81.58 | 0.14 |
| Run # 12 | 4.35 | 7.37 | 4.65 | 8.75 | 30.94 | 15.43 | 28.50 | 46.37 | 13.40 | 74.87 | 0.18 |
| Run # 13 | 2.84 | 5.67 | 3.02 | 6.99 | 18.27 | 26.97 | 36.24 | 45.24 | 10.01 | 81.48 | 0.12 |
| Run # 14 | 2.63 | 4.78 | 3.22 | 7.40 | 19.28 | 26.22 | 36.46 | 45.50 | 10.62 | 81.96 | 0.13 |

TABLE 3 lists results from other analyses. Data are shown graphically in FIGS. 7-10.

| Run # | KF (% water) | UV at 265 nm[#] | CAN[#] | TAN[#] | PhAN[#] | [CO][#] (mmol/g) | C[#] | H[#] | N[#] | O[#] | H/C elemental ratio | O/C elemental ratio |
|---|---|---|---|---|---|---|---|---|---|---|---|---|
| FP-Feed | 26.01 | 0.757 | 82.6 | 209.5 | 126.9 | 4.7 | 62.03 | 7.26 | 0.07 | 30.65 | 1.39 | 0.42 |
| Run # 2 | 54.15 | 0.356 | 80.7 | 145.5 | 64.8 | 3.6 | 59.46 | 11.38 | 0.12 | 29.04 | 2.28 | 0.42 |
| Run # 3 | 51.24 | 0.412 | 89.6 | 157.9 | 68.3 | 3.9 | 58.49 | 11.30 | 0.11 | 30.10 | 2.30 | 0.44 |
| Run # 4 | 48.11 | 0.353 | 74.7 | 139.3 | 64.6 | 4.3 | 56.86 | 10.59 | 0.10 | 32.45 | 2.22 | 0.49 |
| Run # 5 | 50.39 | 0.330 | 71.9 | 128.8 | 56.9 | 4.5 | 56.75 | 11.63 | 0.11 | 31.51 | 2.44 | 0.48 |
| Run # 6 | 49.85 | 0.337 | 95.1 | 165.1 | 70.0 | 5.0 | 60.06 | 11.54 | 0.11 | 28.29 | 2.29 | 0.40 |
| Run # 7 | 45.91 | 0.357 | 85.4 | 157.1 | 71.7 | 4.8 | 57.76 | 10.75 | 0.10 | 31.39 | 2.22 | 0.47 |
| Run # 8 | 43.69 | 0.391 | 73.0 | 137.6 | 64.7 | 4.1 | 57.12 | 10.44 | 0.09 | 32.35 | 2.18 | 0.49 |
| Run # 9 | 41.66 | 0.432 | 74.9 | 154.5 | 79.6 | 4.2 | 59.50 | 9.72 | 0.09 | 30.69 | 1.95 | 0.44 |
| Run # 10 | 45.10 | 0.416 | 79.4 | 154.7 | 75.3 | | | | | | | |
| Run # 11 | 49.47 | 0.362 | 69.2 | 143.1 | 73.8 | | | | | | | |
| Run # 12 | 51.51 | 0.387 | 91.1 | 163.4 | 72.3 | | | | | | | |
| Run # 13 | 54.92 | 0.395 | 71.9 | 143.9 | 72.0 | | | | | | | |
| Run # 14 | 53.80 | 0.379 | 69.7 | 137.7 | 68.0 | | | | | | | |

[#]corrected to dry weight

Data indicate that phenolic groups in the bio-oil were electrochemically reduced. For example: a) the C/H ratio increases to a value of about 2. The increase is attributed to aromatic ring reduction; b) integration of $^{13}C$ NMR spectra shows that aromatic carbons decrease, aliphatic carbons increase, alcohol and ether carbons increase, and the aromatic-to-aliphatic ratio decreases substantially; c) acidity from phenol groups decreases as determined with the phenolic acid number (PhAN); d) UV-VIS spectra show that the absorbance at 265 nm (associated with phenol groups) decreases (see FIGS. 8A-8B); e) UV-VIS and PhAN analyses are consistent with a decrease in phenols of about 50% in the electrochemically treated bio oil; f) the O/C ratio suggests that while deoxygenation does not occur, more oxygen is in the form of alcohols rendering deoxygenation by simple dehydration may be facile in treated bio-oils; and g) carbonyl analysis suggests that a fraction of carbonyl groups are electrochemically hydrogenated (see, e.g., FIG. 10). For example, in Run #2 (TABLE 3), the feed bio oil with a carbonyl (CO) concentration of 4.7 mmol/g was reduced to 3.0 mmol/g for a concentration reduction of about 36 mol %. Run #4 produced a carbonyl concentration reduction of about 45%.

Example 4

Alternate Anode Reaction

EXAMPLE 4 demonstrates an alternate anode reaction in the electrochemical system other than water oxidation for treatment of bio-oil at near ambient pressure. In particular, gases produced in the cathode chamber including, for example, $H_2$ and water vapor are fed to the anode chamber where $H_2$ is oxidized to protons. The PEM electrolyzer of FIG. 2 was employed with a single CEM. In this example, the anode consisted of a sintered titanium plate electroplated with platinum. The cathode employed a catalyst selected from palladium, copper, or nickel supported on a fine carbon powder substrate, which was applied to the membrane. The cell was heated to temperatures up to 80° C. The bio oil was contained in a heated catholyte gas liquid separator vessel at temperatures up to 80° C. Continuous stirring of the bio-oil (cathode) vessel homogenized the bio-oil during processing. Bio-oil was pumped to the cathode side of the electrolyzer where it underwent ECH, and was returned to the cathode gas liquid separator vessel. Gases generated during operation and vapors (e.g., $H_2$ and $H_2O$) were directed to the anode chamber. In addition to the cathode vapors, anode was fed with a controlled flow of liquid water to maintain membrane moisture while minimizing water transport across the membrane. Anode flow was not recirculated. This setup minimized addition of water to the bio-oil as water moved across the membrane in the single membrane cell. Minimization of added water to the bio-oil minimizes bio-oil phase separation.

While exemplary embodiments of the present invention have been shown and described, it will be apparent to those skilled in the art that many changes and modifications may be made without departing from the invention in its true scope and broader aspects. The appended claims are therefore intended to cover all such changes and modifications as fall within the scope of the present invention.

What is claimed is:

1. A process for electrochemical hydrogenation of a complex bio-oil, the process comprising the steps of:
   introducing a feed comprising the complex bio-oil into an electrolysis cell having electrodes operatively coupled to a pair of ion-selective membranes arranged in a zero-gap arrangement to define a center compartment between an anode exchange membrane in contact with the feed comprising the complex bio-oil and a cathode exchange membrane in contact with water; and
   passing a current through the electrolysis cell to obtain protons from the water and short organic acids from the complex bio-oil by converting molecules in the feed to reduced products comprising reduced molecules containing a higher proportion of hydrogen than molecules in the feed while capturing the short organic acids in the center compartment,
   wherein the complex bio-oil comprises numerous different organic and inorganic compounds including esters, acids, aldehydes, alcohols, ketones, sugars, and phenol derivatives,
   wherein the electrochemical hydrogenation removes reactive species and upgrades the complex bio-oil so as to make the reduced products suitable for introduction into a transportation fuel processing system, and
   wherein the electrochemical hydrogenation is conducted without use of a supporting electrolyte or external hydrogen.

2. The process of claim 1, wherein introducing the feed includes flowing the feed continuously into the electrolysis cell.

3. The process of claim 1, wherein the current is varied.

4. The process of claim 1, further including passing the reduced products through a thermal hydrotreating reactor to further increase a proportion of hydrogen in the reduced product.

5. The process of claim 1, further including passing the reduced products to a thermal alcohol dehydration reactor to decrease an oxygen content in the reduced product.

6. The process of claim 1, further including passing the reduced products to a thermal alkylation reactor to increase an average molecular weight of the reduced product.

* * * * *